United States Patent
Kwun et al.

(10) Patent No.: US 7,610,791 B2
(45) Date of Patent: Nov. 3, 2009

(54) TIME-GAIN CONTROL METHOD AND SYSTEM FOR LONG-RANGE GUIDED-WAVE INSPECTION AND MONITORING

(75) Inventors: Hegeon Kwun, San Antonio, TX (US); Ronald H. Peterson, Helotes, TX (US)

(73) Assignee: Southwest Research Institute, San Antonio, TX (US)

( * ) Notice: Subject to any disclaimer, the term of this patent is extended or adjusted under 35 U.S.C. 154(b) by 489 days.

(21) Appl. No.: 11/715,655

(22) Filed: Mar. 8, 2007

(65) Prior Publication Data

US 2007/0225930 A1 Sep. 27, 2007

Related U.S. Application Data

(60) Provisional application No. 60/780,759, filed on Mar. 9, 2006.

(51) Int. Cl.
*G01M 19/00* (2006.01)
(52) U.S. Cl. .............................. 73/1.82; 73/631; 73/598
(58) Field of Classification Search ....................... None
See application file for complete search history.

(56) References Cited

U.S. PATENT DOCUMENTS

| | | | | |
|---|---|---|---|---|
| 4,016,750 A | * | 4/1977 | Green | 73/629 |
| 4,584,880 A | * | 4/1986 | Matzuk | 73/609 |
| 5,773,984 A | | 6/1998 | Suyama et al. | |
| 6,571,634 B1 | | 6/2003 | Bazarov et al. | |
| 6,597,997 B2 | | 7/2003 | Tingley | |
| 6,867,729 B2 | | 3/2005 | Berry et al. | |
| 6,896,171 B2 | | 5/2005 | Den Boer et al. | |
| 6,925,881 B1 | | 8/2005 | Kwun et al. | |
| 6,968,727 B2 | | 11/2005 | Kwun et al. | |
| 2005/0182613 A1 | | 8/2005 | Kwun et al. | |

OTHER PUBLICATIONS

Wilcox, Paul D.; A Rapid Signal Processing Technique to Remove the . . . from Guided Wave Signals; IEEE Transactions on Ultrasonics . . . Frequency Control; V. 50, No. 4, Apr. 2003.
Predoi, Mihai V. et al.; Ultrasonic Inspection of Defects in Welded Plates and Tubes; 1997 IEEE Ultrasonics Symposium; pp. 845-848; Aug. 1997.

(Continued)

*Primary Examiner*—Robert R Raevis
(74) *Attorney, Agent, or Firm*—Kammer Browning PLLC

(57) ABSTRACT

Systems and methods are described that carry out an intelligent, variable, time-gain control (TGC) of signal amplification in a long-range, guided-wave inspection and monitoring system. The systems and methods compensate for signal attenuation over the longer distances that guided-wave inspection techniques are capable of operating with. The sensor signal received is divided into relevant frequency bands that are each subjected to a variable TGC through separate variable gain amplifiers (VGAs). The gain selection is processor controlled through the use of a digital look-up table (LUT) stored with predetermined gain functions and/or data that are both time and frequency specific. The signal components are re-combined and digitized for further signal analysis and defect detection. The LUT is established through one or more methods including a weld signal amplitude equalization approach and a background noise equalization approach.

17 Claims, 5 Drawing Sheets

OTHER PUBLICATIONS

Choi, Myoung-Seon et al.; Transmission Line Model for Simulation of Guided . . . Signals in Piping; IEEE Transactions on Ultrasonics . . . Frequency Control; V. 51, No. 5, May 2004.

Li, Jian et al.; Angular-Profile Tuning of Guided Waves in Hollow Cylinders . . . Phased Array; IEEE Transactions on Ultrasonics . . . Frequency Control; V. 49, No. 12, Dec. 2002.

* cited by examiner

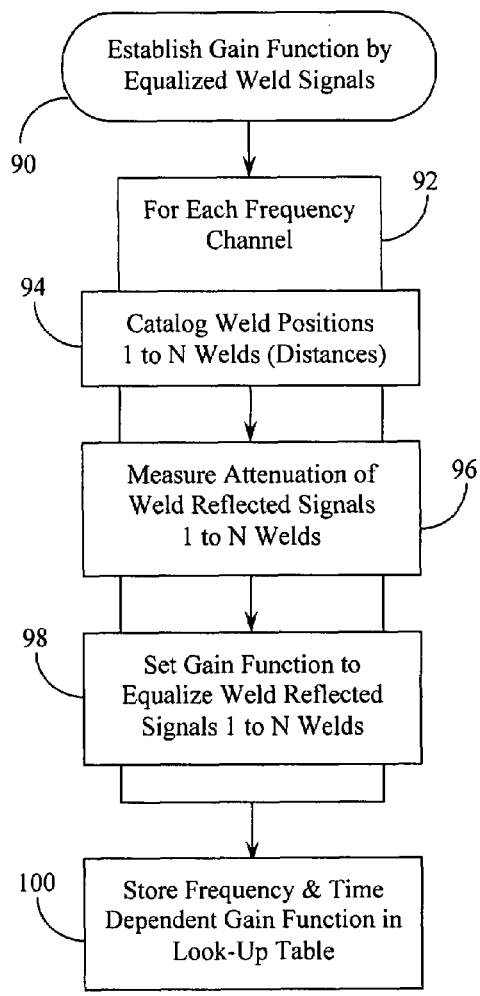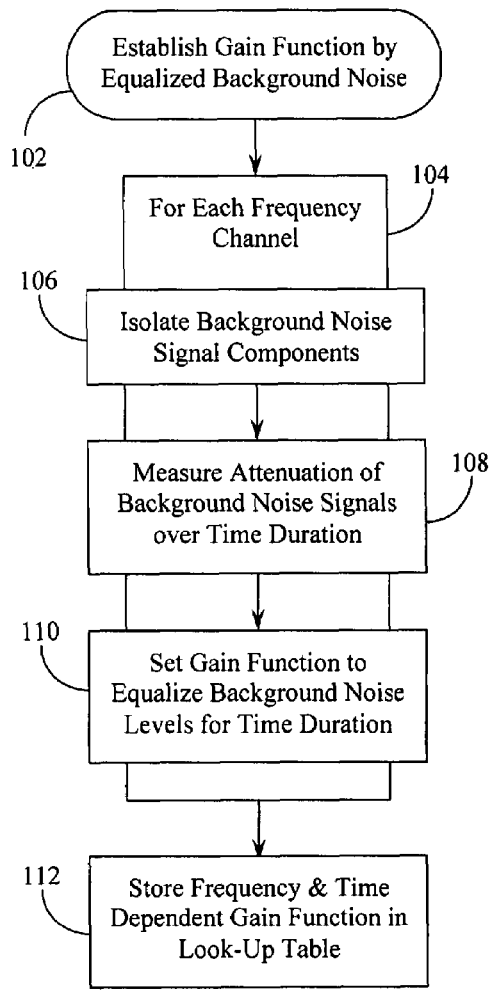
FIG. 5A
FIG. 5B

TIME-GAIN CONTROL METHOD AND SYSTEM FOR LONG-RANGE GUIDED-WAVE INSPECTION AND MONITORING

CROSS REFERENCE TO RELATED APPLICATIONS

This application claims the benefit under Title 35 United States Code § 119(e) of U.S. Provisional Application No. 60/780,759 filed Mar. 9, 2006, the full disclosure of which is incorporated herein by reference.

GOVERNMENT RIGHTS

The U.S. Government has a paid-up license in this invention and the right in limited circumstances to require the patent owner to license others on reasonable terms as provided for by the terms of Contract No.: DTRS56-03-T-0013 awarded by the Department of Transportation (DOT).

BACKGROUND OF THE INVENTION

1. Field of the Invention

The present invention relates generally to methods and devices for the non-destructive evaluation of materials. The present invention relates more specifically to a magnetostrictive sensor based system for the long-range guided-wave inspection of longitudinal structures and a method for compensating for signal attenuation through intelligent variable time-gain control signal amplification.

2. Description of the Related Art

Introduction

The ongoing ability of structural components to function in their intended manner often depends upon the maintenance of their material integrity. Various techniques are used to investigate and monitor the integrity of longitudinal structural objects. Non-Destructive Evaluation (NDE) techniques are important tools to accomplish this investigation and monitoring. NDE techniques range from ultrasonic test systems and methods to electromagnetic (EM) test systems and methods. A highly beneficial feature for some NDE techniques is their ability to investigate and monitor a large (especially long) structure from a single point or a small number of points on the structure. Many such "large structures" are longitudinal in nature (pipes, cables, tubes, plates, and conduits for example). Such structures present specific problems for the investigation and/or monitoring of locations as much as 100 feet or more from the placement of a sensor in an NDE type system.

Long-Range Guided-Wave Inspection

Long-range guided-wave inspection of structures is a recently developed NDE inspection technology that can examine a long length (such as 100 feet) of a longitudinal structure (such as pipes, tubes, steel cables, and plates) quickly, and therefore economically, from a given sensor location. At present, there are two well established guided-wave inspection technologies. One is commonly referred to as magnetostrictive sensor (MsS) technology, and has been pioneered by Southwest Research Institute (SwRI) of San Antonio, Tex. (SwRI is the Assignee of a series of U.S. patents covering MsS based Long-Range Guided-Wave Inspection techniques, including U.S. Pat. Nos. 5,456,113, 5,457,994, 5,581,037, 5,767,766, 6,212,944, 6,294,912, 6,396,262, 6,429,650, 6,624,628, 6,917,196, and as well as additional patents pending).

An example of the functionality of MsS Systems, as described above, can be found in U.S. Pat. No. 6,917,196 issued to Kwun et al. on Jul. 12, 2005 entitled Method and Apparatus Generating and Detecting Torsional Wave Inspection of Pipes and Tubes. This patent describes one approach for implementing MsS Techniques for the NDE of pipes or tubes. In this case, a MsS generates guided-waves which travel in a direction parallel to the longitudinal axis of the pipe or tube. This is achieved (in this particular sensor system) by using a magnetized ferromagnetic strip pressed circumferentially against the pipe or tube. The guided-waves are generated in the strip, are coupled to the pipe or tube, and propagate along its length. Detected guided-waves are coupled back to the thin ferromagnetic strip and may include reflected waves representing defects in the pipe or tube. The full disclosure of U.S. Pat. No. 6,917,196 is incorporated herein by reference.

A second NDE technique used in conjunction with longitudinal structures is commonly referred to as Lamb wave inspection technology. Commercial systems implementing such techniques are marketed under the names Teletest® and Wavemaker®. These systems have been developed by the Imperial College of Science, Technology of Medicine of London, England. These techniques are typified by the system described in U.S. Pat. No. 6,148,672 entitled Inspection of Pipes issued to Crawley et al. on Nov. 21, 2000 and assigned to Imperial College of Science, Technology of Medicine.

The MsS based systems described above generate and detect guided-waves in ferromagnetic materials (such as carbon or alloyed steel) without requiring direct physical contact to the material. Lamb wave based systems on the other hand, generate and detect guided-waves by coupling the waves to an array of piezoelectric sensors in direct physical contact to the material. The MsS is applicable for inspection of various structures including pipes, tubes, plates, and steel cables, whereas the Lamb wave method is primarily used for inspection of pipe from the outside. Both technologies are now in commercial use.

There are a number of advantages to using the magnetostrictive effect in generating and detecting guided-waves for NDE applications. These advantages include; (a) the sensitivity of the magnetostrictive sensors, (b) the mobility of the magnetostrictive sensors, (c) the absence of a need to couple the sensor to the material being investigated, (d) the long-range of the mechanical waves in the material under investigation, (e) the ease of implementation, and (f) the low cost of implementation. The use of magnetostrictive sensors (MsS) in the NDE of materials has proven to be very effective in characterizing defects, inclusions, and corrosion within various types of ferromagnetic and non-ferromagnetic structures. Since guided-waves can propagate long distances (typically 100 feet or more) the magnetostrictive sensor technology can inspect the global volume of a structure very quickly. In comparison, other conventional NDE techniques, such as ultrasonics and EMAT current, inspect only the local area around the sensor.

In general, guided-wave inspection and monitoring techniques involve launching a pulse of guided-waves along the length of pipe and detecting signals reflected from defects such as corrosion damage or cracks back to the position from which the original wave was transmitted. A system for carrying out such an inspection or monitoring of a structure is shown in FIG. 1 and described in more detail below. From the occurrence time of the defect signal and the signal amplitude, the axial location and severity of the defect may be determined. The magnetostrictive sensor based guided-wave inspection technique can afford a 100% volumetric inspection of a long length of piping and has been used effectively on more than 500 feet of straight piping structure in one direction above ground with painting, from a single probe location. Such guided-wave inspection systems are therefore particularly useful for remote inspection of difficult-to-access areas (such as those under insulation or at high elevations) by launching and detecting waves from a remote but accessible location.

Return Signal Analysis—Compensating for Attenuation

Guided-wave inspection techniques can provide comprehensive information on piping conditions with minimal preparation and inspection time. These systems are therefore gaining rapid acceptance as cost-effective inspection methods in various industries including gas, oil, petrochemical, and electric power, where piping is a primary component of the equipment and facilities that serve to transport the product across great distances. One difficulty associated with the inspection or monitoring of longitudinal structures of significant length involves the attenuation of the amplitude of the propagated and reflected signals over distance and time. Because of this attenuation, the guided-waves propagating in a structure become progressively smaller in amplitude the further the waves propagate. If the attenuation is constant, the signal amplitude would decrease exponentially with time or, equivalently, with the traveling distance. Consequently, the guided-wave signals (or echoes) from similar reflectors in a structure (such as girth welds in piping) appear smaller as their distance from the guided-wave probe increases. To maintain the detection sensitivity of the guided-wave so as to be approximately the same over its testing range and, thus, to facilitate subsequent data analyses and interpretation, it is desirable to correct (or compensate for) the attenuation effects on the detected signals.

To achieve the attenuation correction mentioned above, ultrasonic testing systems use a method called time-gain control (TGC), also known as time-gain compensation, time-controlled gain, time-corrected gain, distance-gain control, etc. Since ultrasonic testing systems are used primarily for the short-range (a few feet), local examination of materials, TGC methods employed in these systems do not directly translate as suitable for long-range guided-wave inspection systems. TGC as used with short-range ultrasonic type systems is able to make certain assumptions about the character and structure of the material being inspected that cannot be made with the longer distances of irregular structures that are often inspected and monitored with guided-wave systems.

The purpose of the present invention therefore is to provide systems and methods for the application of time-gain control techniques to long-range guided-wave inspection and monitoring systems. It is therefore an object of the present invention to provide systems and methods that condition a sensor signal from a guided-wave inspection or monitoring system so as to improve the discrimination of defect signals and therefore the detection and location of defects in the structure under investigation.

SUMMARY OF THE INVENTION

In fulfillment of the stated objectives the present invention provides systems and methods that carry out an intelligent, variable, time-gain control (TGC) of signal amplification in a long-range, guided-wave inspection and monitoring system. The systems and methods compensate for signal attenuation over the longer distances that guided-wave inspection techniques are capable of operating with. A sensor signal received is divided into relevant frequency bands that are each subjected to a variable TGC through separate variable gain amplifiers (VGAs). The gain selection is processor controlled through the use of a digital look-up table (LUT) stored with predetermined gain functions that are both time and frequency specific. The signal components are re-combined and digitized for further signal analysis and defect detection. The LUT data of the present invention may be established through one or more methods described including a weld signal amplitude equalization approach and a background noise equalization approach.

BRIEF DESCRIPTION OF THE DRAWINGS

FIGS. 5A & 5B are flowcharts describing alternative approaches to establishing the gain function and look-up table used in the intelligent attenuation compensation method of the present invention.

DETAILED DESCRIPTION OF THE PREFERRED EMBODIMENTS

Figure 1:
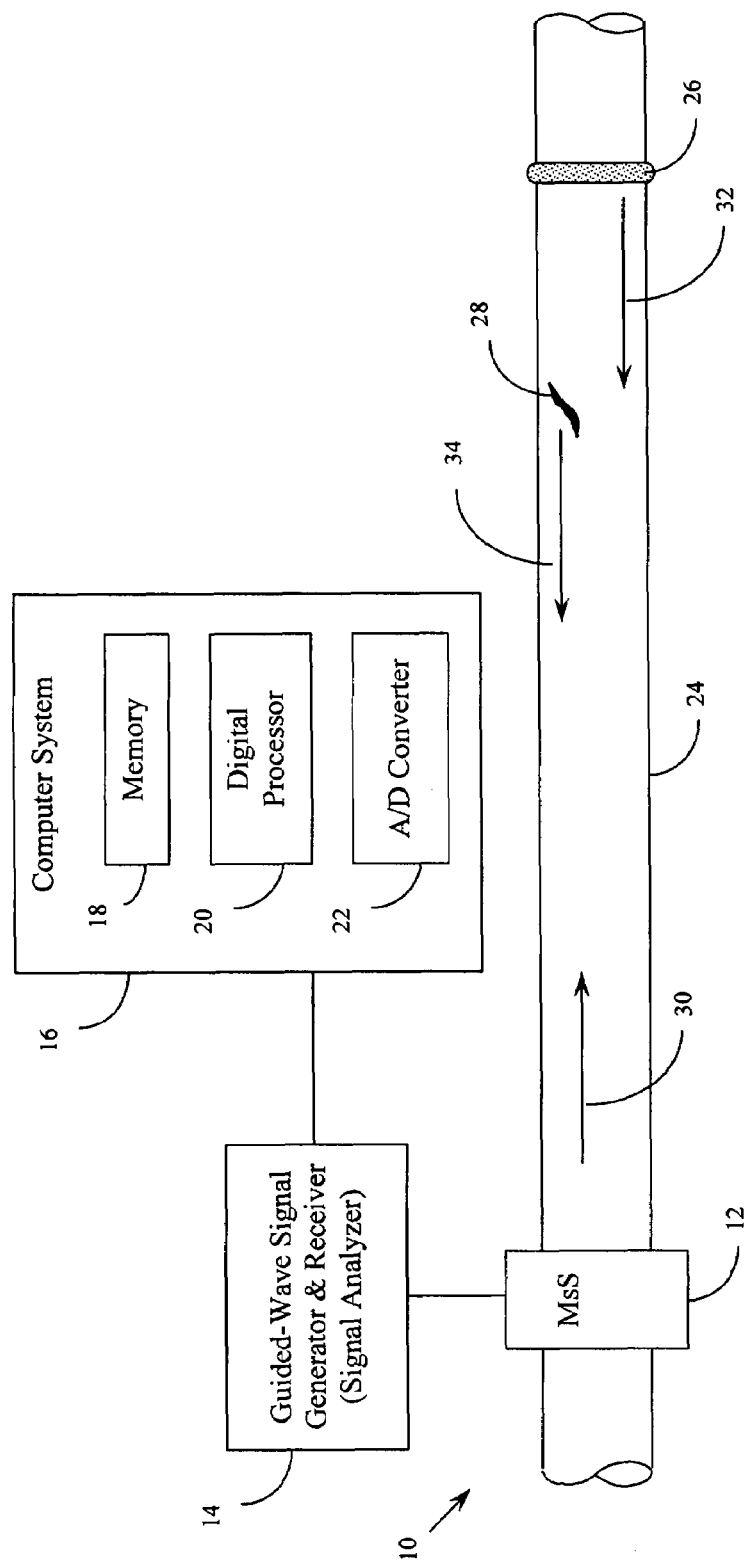
FIG. 1 is a partial schematic diagram showing the primary components of a system appropriate for implementing the methods of the present invention.

Reference is made to FIG. 1 for a brief description of a system appropriate for implementing the methodology of the present invention. References herein to guided-wave systems based on the use of magnetostrictive sensors are provided by way of example and are understood to equally apply to the application of other mechanisms for establishing guided-waves within a structure. Long-range guided-wave inspection system 10 is configured to generate guided-waves within the longitudinal structure shown, and to receive back reflected signals from various anomalies and other intended geometrical elements within the longitudinal structure.

Inspection system 10, as shown in FIG. 1, comprises magnetostrictive sensor component 12 positioned in proximity to longitudinal structure 24, which in this instance may be a longitudinal steel pipe or the like. Inspection system 10 further includes guided-wave signal generator 14 which includes the appropriate electronics to drive the magnetostrictive sensor 12 and to thereby generate the guided-waves within the longitudinal structure 24. Also associated with inspection system 10 is computer system 16 which generically comprises memory 18, digital processor 20, and analog to digital conversion electronics 22. Suitable data storage components (not shown) may also be relevant for processing methodologies associated with the present invention.

As described in the various magnetostrictive sensor and inspection system patents mentioned above, inspection system 10, by way of magnetostrictive sensor 12, generates guided-waves 30 within longitudinal structure 24. Guided-waves 30 travel along the length of and within the material of longitudinal structure 24, until they encounter "anomalous" elements within the structure. These anomalous elements could take the form of intended geometric features, such as weld 26, or could take the form of unintended defect features such as crack 28. In either case, reflected waves, represented as reflected waves 32 and 34, propagate back from these elements and are detected by magnetostrictive sensor component 12 where they are received into the signal analyzer components 14 of the inspection system 10.

Figure 2:
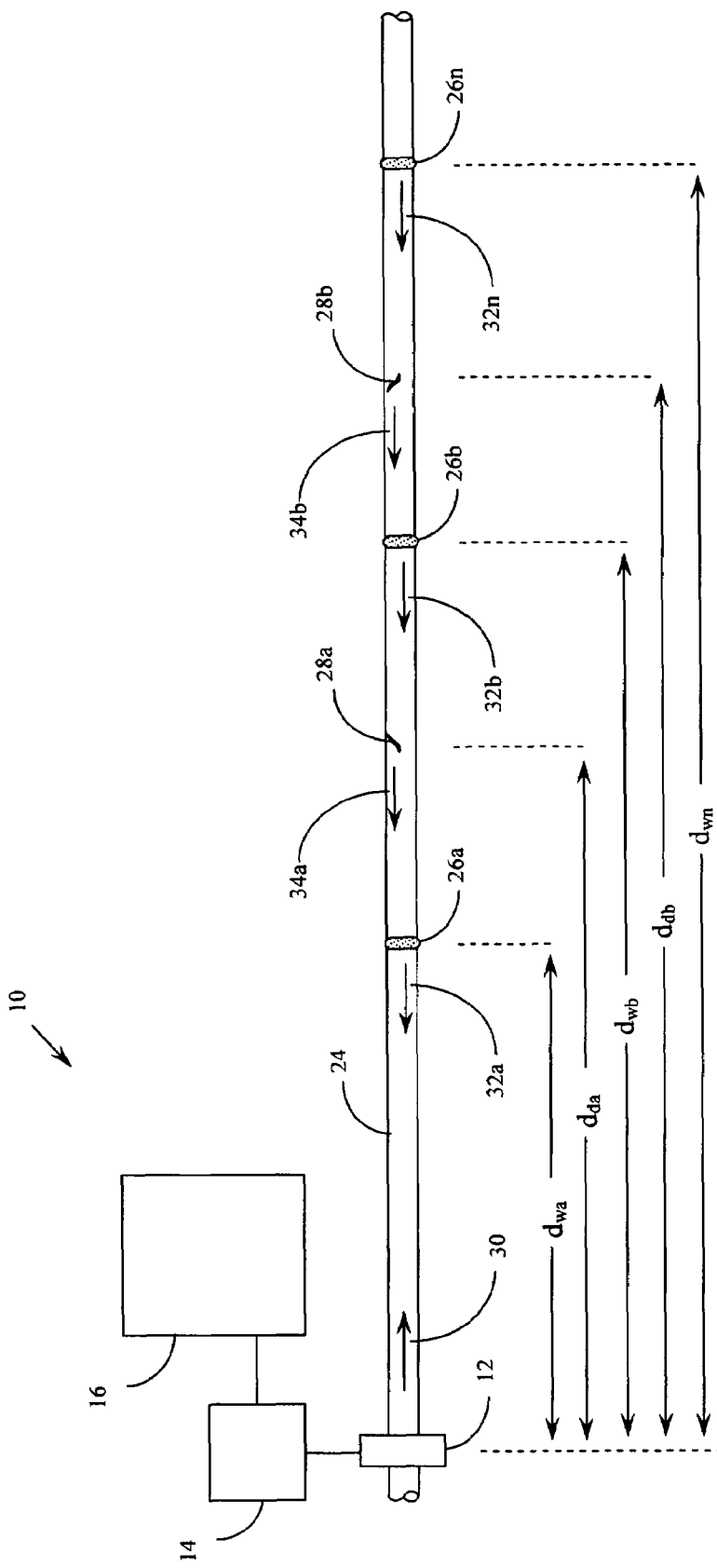
FIG. 2 is a partial schematic diagram (similar to that shown in FIG. 1) of an extended section of pipe showing various sources of reflected signals positioned at increasing distances from the sensor structure of the present invention.

FIG. 2 is a partial schematic diagram (similar to that shown in FIG. 1) of an extended section of pipe showing various sources of reflected signals positioned at increasing distances from the sensor structure of the present invention. In this view a number of "anomalous" elements are seen spaced at various distances, each having a reflected signal whose amplitude is subject to attenuation, both as a result of the attenuation of the incident wave and of the reflected wave. In this example, a number of welds $26a, 26b \ldots 26n$ positioned at distances $d_{wa}$, $d_{wb}, \ldots d_{wn}$ cause reflected signals $32a, 32b \ldots 32n$ that are each received (with differing attenuations) by sensor 12. In similar fashion, a number of defects (cracks, inclusions, corrosion, etc.) represented by defects $28a$ & $28b$ positioned at distances $d_{da}$ & $d_{db}$ cause reflected signal $34a$ & $34b$ that are also each received (again with differing attenuations) by sensor 12. The methods of the present invention address the various attenuations experienced by the incident and reflected signals traveling to and from these features within the structure under inspection.

Figure 3:
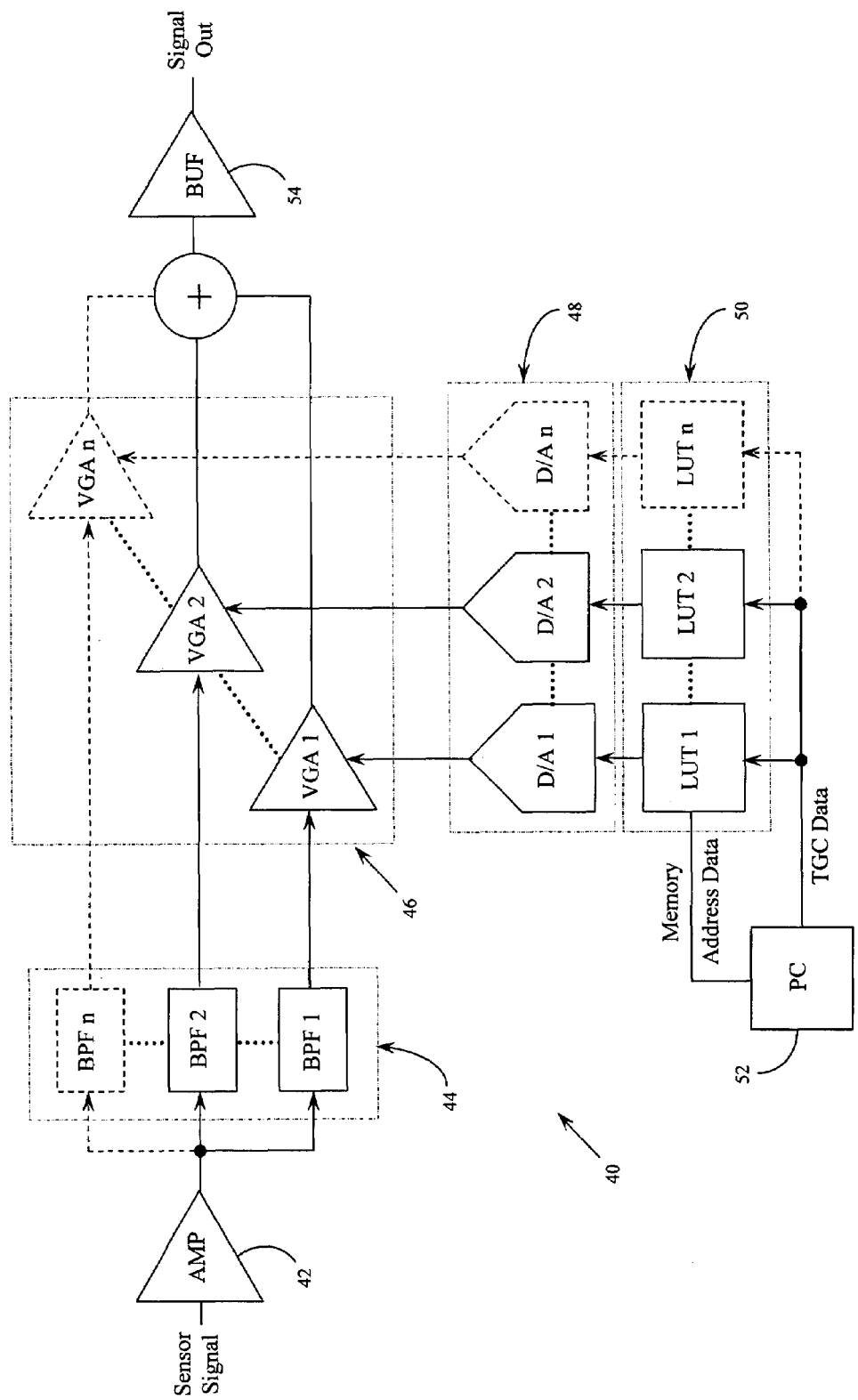
FIG. 3 is an electronic schematic block diagram showing the arrangement of components for carrying out the functionality of the method of the present invention.

FIG. 3 is an electronic block schematic diagram showing an arrangement of electronic components in a preferred embodiment of the present invention, suitable for carrying out the functionality of the methods described herein. The sensor signal received by the guided-wave probe and communicated to the electronic instrumentation 40 of the system is divided into several channels of different frequencies around the operating frequency of the probe. This is accomplished by passing the signal through a parallel set of band-pass filters 44 represented by BPF 1, BPF 2 ... BPF n. Signals in each channel, now within selected frequency bands, are then processed through a variable TGC arrangement of electronic components as described in more detail below. Processed signals from all channels are then recombined to provide a single signal output.

The MsS guided-wave signal input to the TGC circuit 40 is shown at the upper left side of FIG. 3. This signal is normally the sum of signals received from two or more sensors phase-aligned to produce directionality. The signal may be level-adjusted by a fixed gain or programmable (operator-selected) gain amplifier (AMP) 42. As described above, the signal is then applied to a set of analog band-pass filters (BPFs) 44 that separate the signal into discrete frequency bands. Subsequently, the signals in each band are again amplified using a set of parallel variable-gain amplifiers (VGAs) 46 with a time-dependent gain function unique to the band. The source of this time-dependent gain function is described in more detail below. The signals from all of the VGAs 46 are then summed and preferably passed to a buffer amplifier 54 before being digitized by an analog-to-digital converter (not shown) for subsequent intelligent processing.

The gain of each VGA 46 is preferably controlled by an applied analog voltage signal. In FIG. 3, these control signals are shown to be generated through a set of parallel digital-to-analog (D/A) converters 48 whose input data come from a digital look-up table (LUT) 50. The LUT (or LUTs as necessary) 50 stores a time-dependent gain function for each of the specific frequency bands. The LUT data are converted to the analog control voltage signal synchronous with the initiation of the MsS signal. A personal computer (PC) 52 or other processing component loads the LUT(s) 50 with data based on a calibration procedure that determines the gain function required to normalize the attenuation rate of each frequency band. A further aspect of the method of the present invention involves techniques for establishing the appropriate gain function for each of the frequency bands. These techniques are described in more detail below.

In general, the wave attenuation along a structure such as piping is not constant, but varies as the character and condition of the piping system varies. As an example, some sections of pipe may be newly replaced, may have damping elements in place (such as bitumen coating or composite wraps), may be underground, or may be exposed to a more corrosive environment. The use of variable TGC allows for the system to correct the varying attenuations in different regions of the structure under inspection. If the structure under inspection has a relatively uniform attenuation along its length, the TGC would be set to a constant rate. However, because wave attenuation is frequency-dependent (in general, the higher the wave frequency, the higher the attenuation) it is also necessary to account for signal components of different frequencies. If the attenuation is highly frequency-dependent in the frequency band of the guided-wave pulse, the shapes of the detected signals change significantly with distance (or time). An example of such an effect can be seen in the case of wave attenuation in bitumen-coated pipelines. Studies have shown for instance, attenuations of 0.08 dB/ft at 10 kHz, 0.18 dB/ft at 20 kHz, and 0.33 dB/ft at 30 kHz for a torsional wave propagating in the pipeline. The selection of the frequency bands is therefore a matter of selecting ranges of frequencies around the frequency of the incident wave that will cover those reflected wave frequencies anticipated from both the defect sources and the intended geometric sources in the pipeline.

Figure 4:
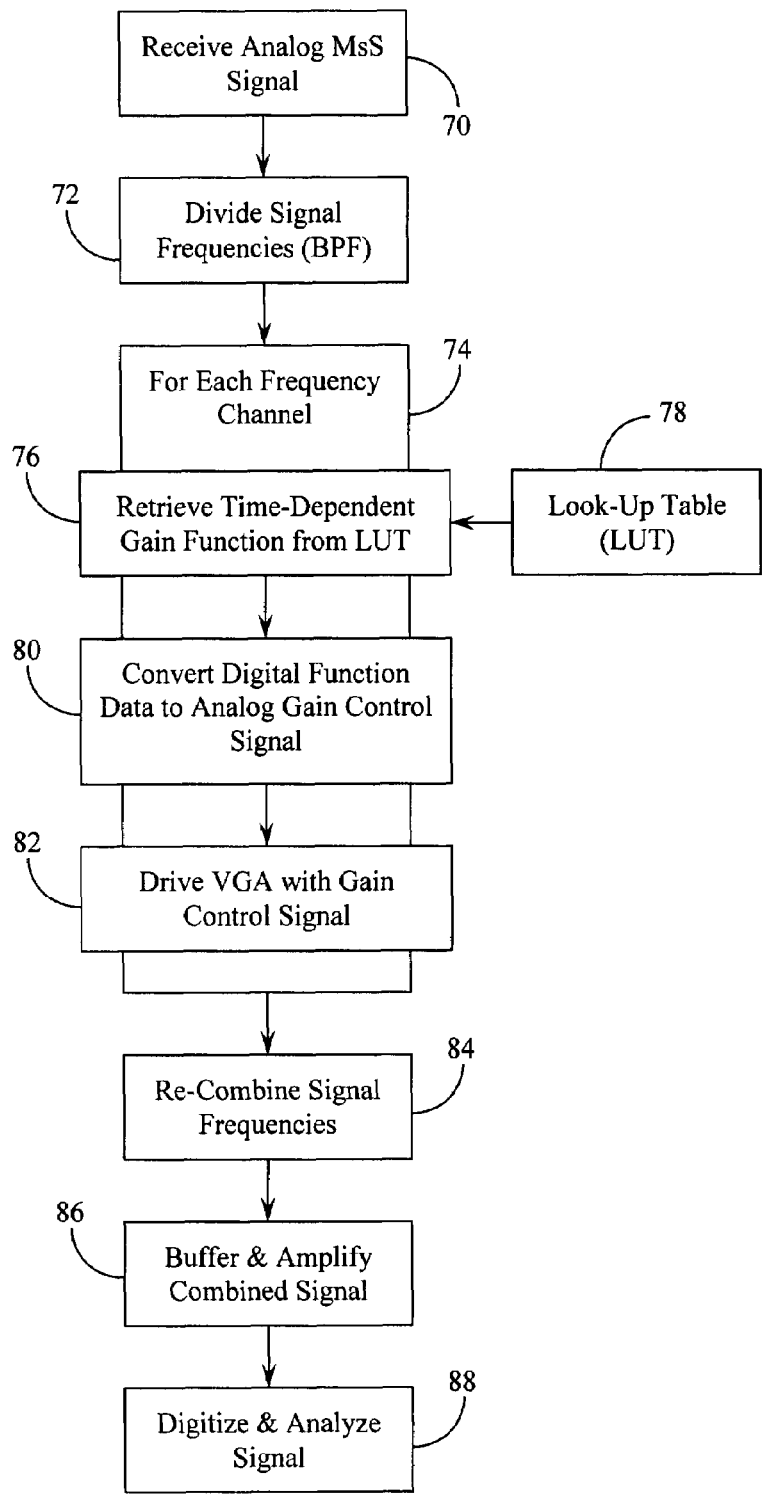
FIG. 4 is a flowchart describing the general steps in the intelligent attenuation compensation method of the present invention.

Reference is now made to FIG. 4 for a description of the general steps in the intelligent attenuation compensation method of the present invention. The method steps shown in FIG. 4 generally follow the operation of the electronics disclosed and described in association with FIG. 3 above. The process is essentially a signal conditioning process whereby various frequencies within the signal are amplified according to a time and frequency dependent scale. The establishment of the scale (the gain function) is described in more detail below with reference to FIGS. 5A & 5B. The method described herein begins after acquisition of the guided-wave signal from the sensor (the magnetostrictive sensor in the preferred embodiment, for example) and ends with the output of a digital signal (in the preferred embodiment) appropriate for further defect detection analysis.

The method begins at Step 70 wherein the TGC instrumentation receives the analog MsS signal. The sensor signal is divided at Step 72, essentially by providing parallel input to the set of band-pass filters (BPFs) as described above. Step 74 is operative for each of the separate frequency channels associated with each of the BPFs and includes a sequence of steps involving the retrieval of a gain control signal and its application to the separate frequency bands. The time-dependent gain function for each frequency band is retrieved at Step 76 from a look-up table (LUT) established at Step 78. The digital function data is converted to an analog gain control signal at Step 80 and is used to drive the appropriate variable gain amplifier (VGA) at Step 82. The selectively amplified frequency band signals are then re-combined at Step 84 and provided to a buffer amplifier at Step 86. Finally, at Step 88 the re-combined analog signal may be digitized for further signal analysis to identify and characterize the presence of defect features in the structure.

In general, the use of the multiple frequency channels and the application of the variable TGC to each channel, help to reduce the distortion in signal shape. Preserving the signal shape as much as possible is important for defect characterization. To adjust the variable TGC properly, the wave attenuation and its frequency dependence along the length of a structure under inspection need to be characterized. Directly measuring the wave attenuation and its frequency dependence is time consuming and thus expensive, and as a result is most often impractical. In practice, therefore, the information needed to establish a gain function is rarely available for controlling the variable TGC.

In the preferred embodiment of the present invention, two alternative or coordinated approaches to establishing gain functions are used as practical means to control the variable TGC. These approaches include; (1) identifying weld signals and adjusting the variable TGC such that the weld signal amplitudes are approximately the same; and (2) adjusting the variable TGC so that the background noise level is approximately the same throughout the time period (over the distance) under investigation. In the latter approach the background noise refers to a low-level coherent noise from the structure, excluding the signals from defects such as corrosion pits and radio-frequency noise picked up by the guided-wave probe or generated by the guided-wave system instruments. In the preferred methodology of the present invention, when the received signals contain fewer than two weld signals, the second of the two approaches is used.

FIGS. 5A & 5B are flowcharts describing the alternative approaches to establishing the gain functions and look-up table used in the method of the present invention. The first approach, initiated at Step 90 in FIG. 5A, establishes the gain functions by equalizing weld signals received. Step 92 includes a sequence of steps that are carried out for each of the identified and selected frequency channels established in the TGC instrumentation. Initially, at Step 94, the positions of the welds in the piping structure are identified, either by external observation or by analytical techniques for discriminating weld signals from the guided-wave signal interrogation of the piping structure. These welds then become "markers" in the structure that act as references for the degree of attenuation at the marked position. At Step 96 the attenuation level for each of the welds is determined. A gain function is thereby established that equalizes the signal amplitudes for each of the weld signals in the process of Step 98. The gain function may be an actual function (such as an exponential function where the attenuation is constant) or may be more in the nature of a profile that varies in a more complex manner due to unique geometric features in the piping structure. In either case, Step 98 establishes the relationship between time (and therefore distance) and an appropriate gain level to compensate for attenuation of the signal. As indicated above, the use of the methodology involving weld signal equalization is dependent on there being sufficient welds to provide "data points" to characterize the gain function or profile. The process in FIG. 5A concludes with Step 100 wherein the functions/data established are stored in the look-up table for ready access (under processor control) by the TGC circuitry. The following discussion provides an alternate or a coordinated approach to establishing the gain function and look-up table data. That is, these two approaches may be used in concert to establish a single gain function (per frequency) or a single gain profile (per frequency).

The process shown in FIG. 5B is similar to that of FIG. 5A although an effort is made to equalize background signal (noise) levels as opposed to weld signal levels. This second approach, initiated at Step 102 in FIG. 5B, establishes the gain functions by equalizing a second signal feature (the background noise) that can be judged to be relatively constant in character over the length of structure under investigation, but for attenuation effects. Step 104 includes a sequence of steps that are carried out for each of the identified and selected frequency channels established in the TGC instrumentation. Initially, at Step 106, the background noise component of the signal is identified, primarily by discriminating the low-level coherent noise from the structure exclusive of signals from defects and exclusive of RF noise picked up by the guided-wave probe or generated from the guided-wave system instrumentation. The background noise profile then becomes the basis for establishing an attenuation profile. At Step 108 the attenuation levels for the range of investigation (time and/or distance duration) are determined. A gain function is thereby established that equalizes the signal amplitude of the background noise over this range in the process of Step 110. Here again, the gain function may be an actual function or may be more in the nature of a profile. In either case, Step 110 establishes the relationship between time (and therefore distance) and an appropriate gain level to compensate for attenuation of the signal. The process in FIG. 5B concludes with Step 112 wherein the functions/data established are stored in the look-up table for ready access (under processor control) by the TGC circuitry.

The range (or distance) over which the present invention is effective may be up to the distance where the conditions that are used to control TGC in the two above-referenced procedures start to break down. This could begin to occur in the latter case where defect signals become lost in the background noise and are no longer distinguishable, even with TGC. Likewise, sufficiently distant welds may begin to return signals that are indistinguishable from the background noise signal. Efforts have shown, however, that operation of a system implementing the methodologies described can be effective over hundreds of feet of piping structure under appropriate conditions.

In the manner described, the present invention therefore provides systems and methods for compensating for attenuation effects in signal data associated with long-range guided-wave inspections and monitoring. Although the present invention has been described in terms of the foregoing preferred embodiments, this description has been provided by way of explanation only, and is not intended to be construed as a limitation of the invention. Those skilled in the art will recognize modifications of the present invention that might accommodate specific non-destructive evaluation environments and structures. Such modifications, as to interrogating signal character, frequency, amplitude, and even sensor configuration, where such modifications are coincidental to the type of structure being investigated, do not necessarily depart from the spirit and scope of the invention.

We claim:

1. A method for compensating for signal attenuation within a structure in a guided-wave inspection/monitoring system, the method comprising the steps of:
   (a) receiving a guided-wave signal representing return signal components from the propagation and reflection of guided-waves within the structure;
   (b) dividing the guided-wave signal into a plurality of discrete frequency bands; and
   (c) applying frequency specific variable time-gain control (TGC) to each of the frequency bands by reference to predetermined time and frequency specific gain information associated with the structure.

2. The method of claim 1 further comprising the step of:
   (d) recombining the frequency bands into a single attenuation-compensated signal.

3. The method of claim 2 further comprising the step of:
   (e) digitizing the attenuation-compensated signal for further signal analysis and defect detection.

4. The method of claim 1 wherein the step of applying frequency specific variable time-gain control (TGC) to each of the frequency bands comprises the steps of:
provuding separate variable gain amplifiers (VGAs); and
controlling the gain of each of the VGAs by reference to predetermined time and frequency specific gain information associated with the structure.

5. The method of claim 1 wherein the referenced gain information associated with the structure is a time or distance dependent function.

6. The method of claim 1 wherein the referenced gain information associated with the structure is a data set.

7. The method of claim 1 wherein the predetermined time and frequency specific gain information is established by equalizing guided-wave signals received from welds at known locations within the structure.

8. The method of claim 1 wherein the predetermined time and frequency specific gain information is established by equalizing filtered background noise signals received from within the structure.

9. A method for compensating for signal attenuation over long distances within a structure, in a guided-wave inspection/monitoring system, the method comprising the steps of:
(a) receiving a guided-wave signal representing return signal components from the propagation and reflection of guided-waves within the structure;
(b) dividing the received guided-wave signal into a plurality of discrete frequency bands;
(c) applying frequency specific variable time-gain control (TGC) to each of the frequency bands through separate variable gain amplifiers (VGAs), the gain control to each of the VGAs selected by reference to predetermined time and frequency specific gain information associated with the structure;
(d) recombining the amplified frequency bands into a single attenuation-compensated signal; and
(e) digitizing the attenuation-compensated signal for further signal analysis and defect detection.

10. The method of claim 9 wherein the predetermined time and frequency specific gain information is established by equalizing guided-wave signals received from welds at known locations within the structure.

11. The method of claim 9 wherein the predetermined time and frequency specific gain information is established by equalizing filtered background noise signals received from within the structure.

12. A system for compensating for signal attenuation over long distances within a structure, in a guided-wave inspection/monitoring system, the system comprising:
(a) a sensor for receiving guided-wave signals representing return signal components from the propagation and reflection of guided-waves within the structure;
(b) a plurality of band-pass filters for dividing the received guided-wave signal into a plurality of discrete frequency bands; and
(c) a plurality of variable gain amplifiers (VGAs) for applying frequency specific variable time-gain control (TGC) to each of the frequency bands, the gain control of each of the VGAs selected by predetermined time and frequency specific gain information associated with the structure.

13. The system of claim 12 further comprising a pre-amplifier for amplifying the received guided wave signal prior to dividing the signal with said plurality of band-pass filters.

14. The system of claim 12 further comprising an additive signal mixer for recombining the amplified frequency bands into a single attenuation-compensated signal.

15. The system of claim 14 further comprising an analog to digital converter for digitizing the attenuation-compensated signal.

16. The system of claim 12 further comprising:
a plurality of digital memory devices comprising data lookup tables, the lookup tables comprising the predetermined time and frequency specific gain information associated with the structure; and
a plurality of digital to analog converters for converting the digital gain information in the plurality of digital memory devices to analog gain control for each of the VGAs.

17. The system of claim 16 wherein the plurality of digital memory devices comprise virtual sectors of a data storage device addressable by a control microprocessor.

* * * * *